(12) United States Patent
Ying et al.

(10) Patent No.: US 8,268,177 B2
(45) Date of Patent: Sep. 18, 2012

(54) MICROFLUIDIC SEPARATION SYSTEM

(75) Inventors: Jackie Y. Ying, Singapore (SG); Guolin Xu, Singapore (SG); Yoke San Daniel Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 412 days.

(21) Appl. No.: 12/673,160

(22) PCT Filed: Aug. 13, 2008

(86) PCT No.: PCT/SG2008/000300
§ 371 (c)(1),
(2), (4) Date: Feb. 11, 2010

(87) PCT Pub. No.: WO2009/022994
PCT Pub. Date: Feb. 19, 2009

(65) Prior Publication Data
US 2012/0024770 A1    Feb. 2, 2012

Related U.S. Application Data

(60) Provisional application No. 60/935,443, filed on Aug. 13, 2007.

(51) Int. Cl.
*B03C 1/035* (2006.01)
*B81B 1/00* (2006.01)
(52) U.S. Cl. ..... 210/695; 210/222; 436/526; 435/287.3; 209/232
(58) Field of Classification Search ............... 210/695, 210/222; 436/526; 435/287.3; 209/232
See application file for complete search history.

(56) References Cited

U.S. PATENT DOCUMENTS

| | | | |
|---|---|---|---|
| 3,567,026 A | 3/1971 | Kolm | |
| 3,676,337 A | 7/1972 | Kolm | |
| 3,902,994 A | 9/1975 | Maxwell et al. | |
| 4,663,029 A | 5/1987 | Kelland et al. | |
| 5,186,827 A | 2/1993 | Liberti et al. | |
| 5,200,084 A | 4/1993 | Liberti et al. | |

(Continued)

FOREIGN PATENT DOCUMENTS

EP       1661625 A1    5/2006

(Continued)

OTHER PUBLICATIONS

Australian Patent Office, "International Search Report and Written Opinion", mailed Oct. 15, 2008, in PCT patent application No. PCT/SG2008/000300.

(Continued)

*Primary Examiner* — David A Reifsnyder
(74) *Attorney, Agent, or Firm* — Klarquist Sparkman, LLP

(57) ABSTRACT

A microfluidic separation system, which comprises a magnetic separator, which itself comprises a magnetic energy source; first and second magnetically conductive members leading from the magnetic energy source and having respective terminal ends that are separated by a gap over which a magnetic field is applied due to the magnetic energy source. The separation system further comprises a microfluidic chip for insertion into the gap, which comprises a body defining channels on respective faces of the body; and an exterior lining that seals the plurality of channels to allow separate test sample volumes to circulate in at least two of the channels. Upon insertion of the chip into the gap, a first test sample volume is confined to circulating closer to the terminal end of the first member and a second test sample volume is confined to circulating closer to the terminal end of the second member.

27 Claims, 19 Drawing Sheets

U.S. PATENT DOCUMENTS

| | | |
|---|---|---|
| 5,466,574 A | 11/1995 | Liberti et al. |
| 6,471,860 B1 | 10/2002 | Miltenyi et al. |
| 7,056,657 B2 | 6/2006 | Terstappen et al. |
| 2003/0107946 A1 | 6/2003 | Cosby et al. |
| 2005/0148064 A1 | 7/2005 | Yamakawa et al. |
| 2005/0244283 A1 | 11/2005 | Yao et al. |
| 2005/0274650 A1 | 12/2005 | Frazier et al. |

FOREIGN PATENT DOCUMENTS

| | | |
|---|---|---|
| WO | 99/42219 A1 | 8/1999 |
| WO | 03/061835 A1 | 7/2003 |
| WO | 03/072227 A1 | 9/2003 |
| WO | 2006/054991 A1 | 5/2006 |
| WO | 2007/035498 A2 | 3/2007 |
| WO | 2007/044642 A2 | 4/2007 |

OTHER PUBLICATIONS

Australian Patent Office, "International Preliminary Report on Patentability", Jun. 19, 2009, in PCT patent application No. PCT/SG2008/000300.

MICROFLUIDIC SEPARATION SYSTEM

CROSS-REFERENCE TO RELATED APPLICATION

The present application claims the benefit under 35 U.S.C. 119(e) of U.S. Provisional Patent Application Ser. No. 60/935,443 to Ying et al., filed Aug. 13, 2007, hereby incorporated by reference herein.

FIELD OF THE INVENTION

The present invention relates generally to microfluidics and, more particularly, to a microfluidic separation system that comprises a magnetic separator and a microfluidic chip.

BACKGROUND

Microfluidic devices can be used to conduct biomedical research and create clinically useful technology. Particular types of microfluidic devices rely on the use of a magnetic field to separate small volumes of magnetic particles from a larger test sample that is mostly non-magnetic. In the separation process, tiny magnetic particles coated with targeting monomers or polymers (e.g., proteins) are used to specifically bind with targeted material such as cells, nucleic acids and proteins. This allows a wide range of targeted material to be separated from biologically complex test samples.

It is noted that the magnetic force on a magnetic particle is directly dependent on the particle size, the field strength of the magnetic field, and the field gradient of the magnetic field. An increase in particle size, field strength or field gradient would result in an increase in the magnetic force, giving rise to an increased magnetic separation efficiency.

Larger magnetic particles (1-10 µm in diameter) require relatively low magnetic field strength and field gradient for separation. However, they do not form stable colloidal suspensions easily. The large particles would sediment easily and would require continuous stirring of the test sample to prevent sedimentation. Additionally, the surface-to-volume ratio is low for larger magnetic particles compared to smaller ones. This tends to reduce the number of effective binding sites to targets, especially when the targets are present in low density. These various factors lead to low separation efficiency for larger magnetic particles.

On the other hand, smaller magnetic particles (of tens to hundreds of nanometers in diameter) do lend themselves to be synthesized with colloidal stability. However, a high magnetic field strength with a large field gradient is needed to generate sufficient magnetic force on the small magnetic particles.

Commercially available magnetic separators generate a high gradient magnetic field by presenting a matrix with steel wool or ferromagnetic balls to a magnetic field, or by the polarity and positioning of the magnets' location around a container with the test sample. One approach is described in U.S. Pat. Nos. 3,567,026, 3,676,337, 3,902,994 and 6,471,860. In this approach, a plastic column for admitting a flow of the test sample contains a matrix filled with steel wool or ferromagnetic balls of different sizes. This method has disadvantages, such as the non-specific entrapment of biological entities other than the targeted substance. The matrix is also harmful to certain sensitive cell types, and the targeted substance may become contaminated.

A second approach is described in U.S. Pat. Nos. 5,200,084, 4,663,029, 5,466,574 and 7,056,657. This approach comprises sets of 4 to 64 permanent magnets. These magnets are arranged to define a cavity that accommodates a container used for admitting a flow of the test sample. The polarity and positioning of the magnets located on opposite sides of the cavity produce flux lines that generate a high-gradient magnetic field. Although this approach has advantages over the first one using a matrix, it has a complicated structure and a very weak magnetic field at the center of the cavity.

Thus, there is a need in the industry for an improved microfluidic separation system.

SUMMARY OF THE INVENTION

In accordance with a first aspect, the present invention seeks to provide a microfluidic separation system, which comprises:
  a magnetic separator, comprising:
    a. a magnetic energy source;
    b. first and second magnetically conductive members leading from the magnetic energy source and having respective terminal ends; and
    c. the terminal ends of the first and second members being separated by a gap over which a magnetic field is applied due to the magnetic energy source; and
  a microfluidic chip for insertion into the gap, comprising:
    a. a body defining a plurality of channels on respective faces of the body; and
    b. an exterior lining that seals the plurality of channels to allow separate test sample volumes to circulate in at least two of the channels;
  wherein upon insertion of the microfluidic chip into the gap, a first one of the test sample volumes is confined to circulating closer to the terminal end of the first member and a second one of the test sample volumes is confined to circulating closer to the terminal end of the second member.

In accordance with a second aspect, the present invention seeks to provide a microfluidic separation system, which comprises:
  a magnetic separator, comprising:
    a. a first magnetically conductive member having a first terminal end,
    b. a second magnetically conductive member having a second terminal end,
    c. a surface of the first terminal end exhibiting corrugations;
    d. the first and second conductive members being arranged to leave a gap between said terminal ends; and
    e. a magnetic energy source connected to the first and second members and causing a magnetic field to be applied across the gap, wherein the magnetic field exhibits lines of strong magnetic field between tips of the corrugations on the first terminal end and a surface of the second terminal end; and
  a microfluidic chip for insertion into the gap, comprising a body defining a channel including generally parallel elongate traces within a plane of flow that is orthogonal to the lines of strong magnetic field, certain ones of the traces being aligned with respective ones of the lines of strong magnetic field as projected onto said plane.

BRIEF DESCRIPTION OF THE DRAWINGS

In the accompanying drawings.

DETAILED DESCRIPTION

Figure 1:
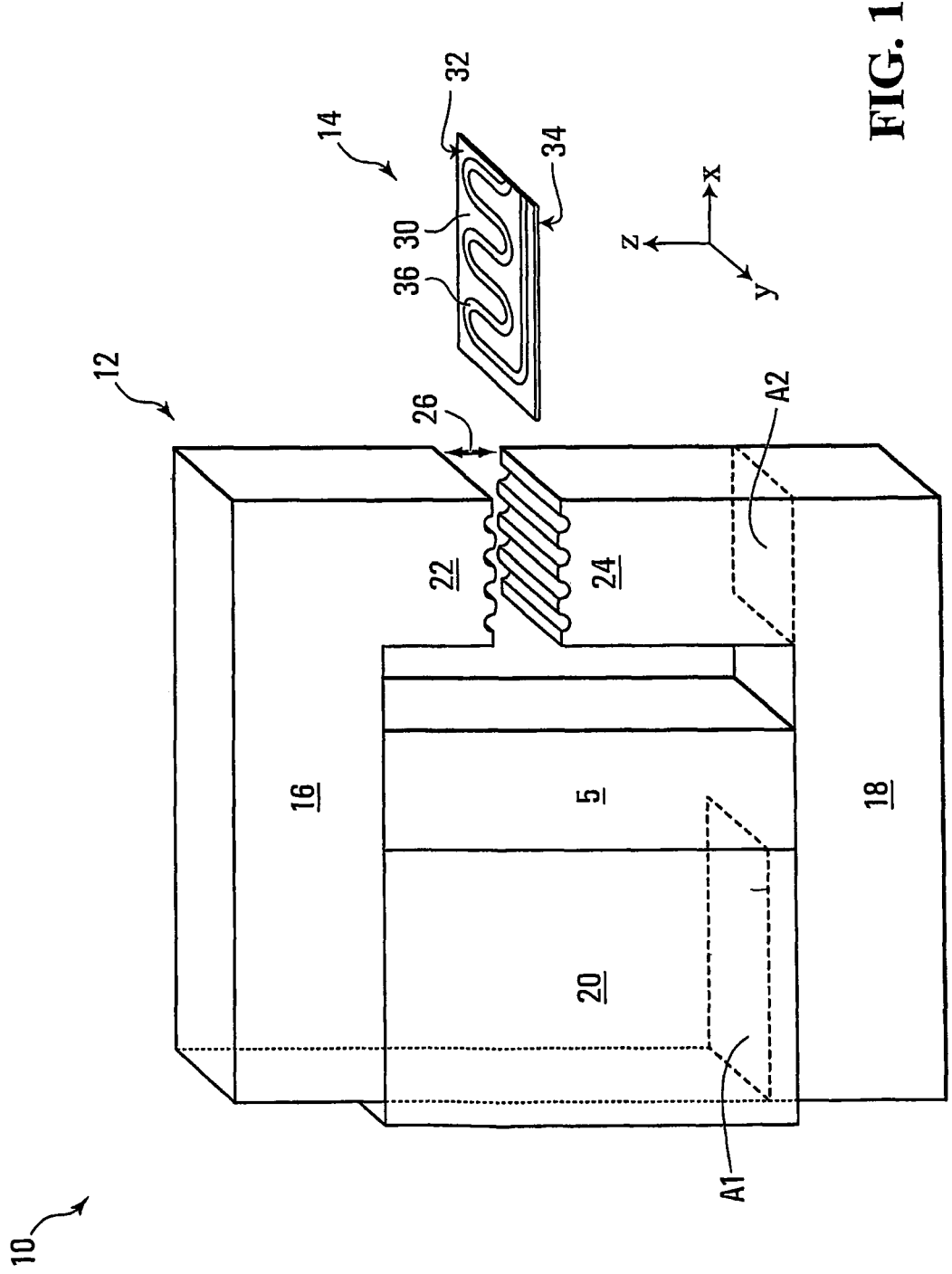
FIG. 1 is a perspective view of a microfluidic separation system that includes a magnetic separator with magnetically conductive members whose terminal ends form a gap, and a microfluidic chip for insertion into the gap.
Figure 2A:
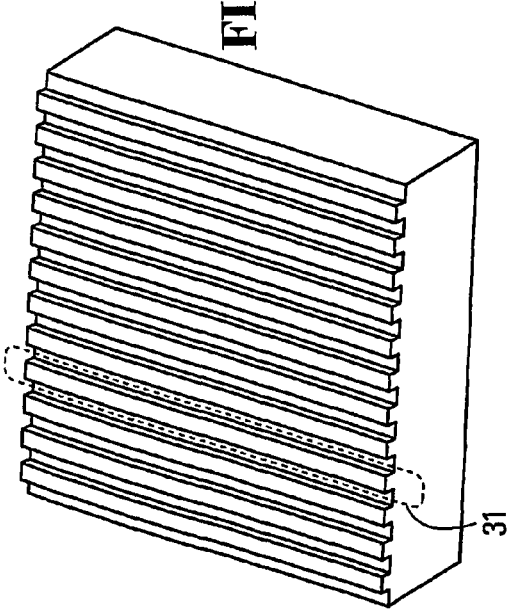
FIGS. 2A-2F show possible surface profiles for one or both of the terminal ends in FIG. 1, in accordance with a non-limiting embodiment of the present invention.
Figure 2B:
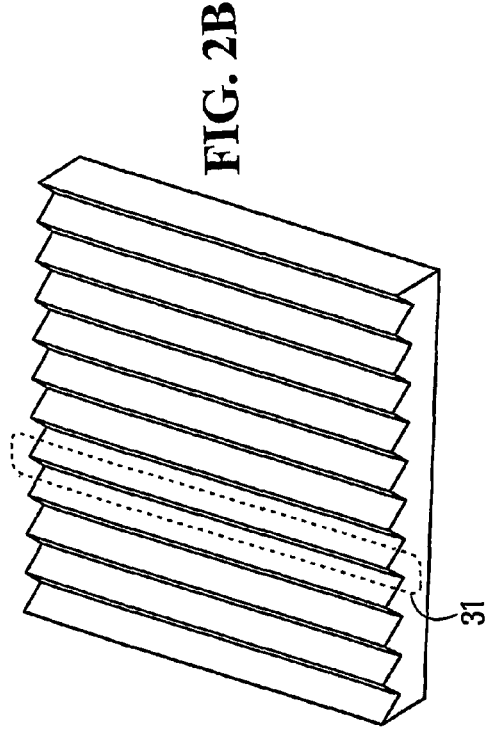
Figure 2C:
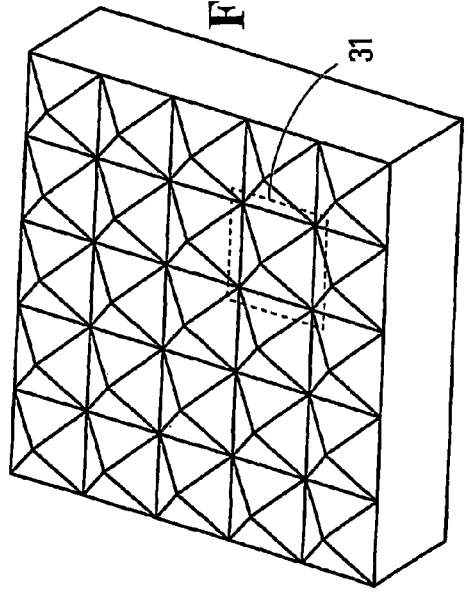
Figure 2D:
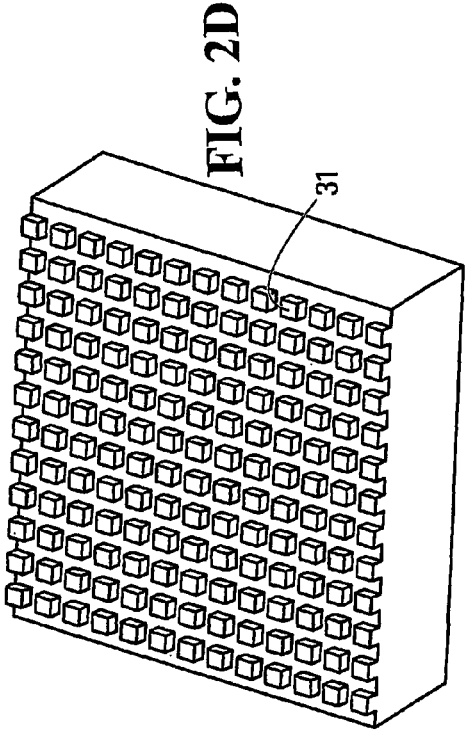
Figure 2F:
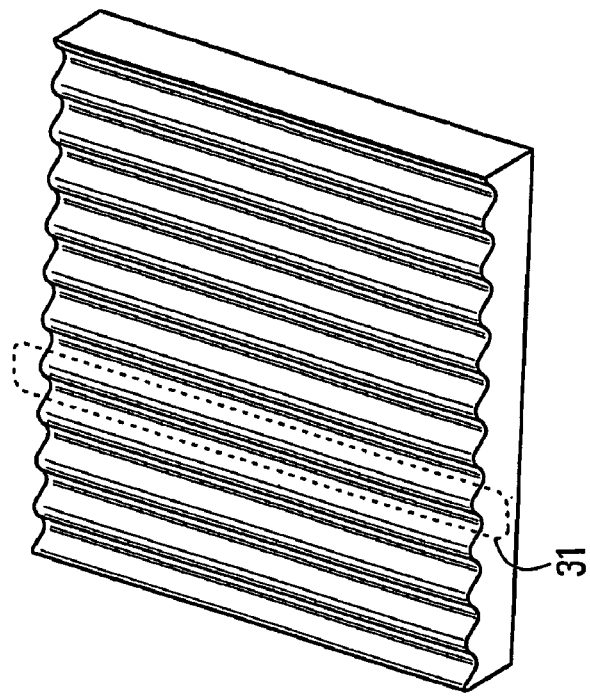
Figure 2E:
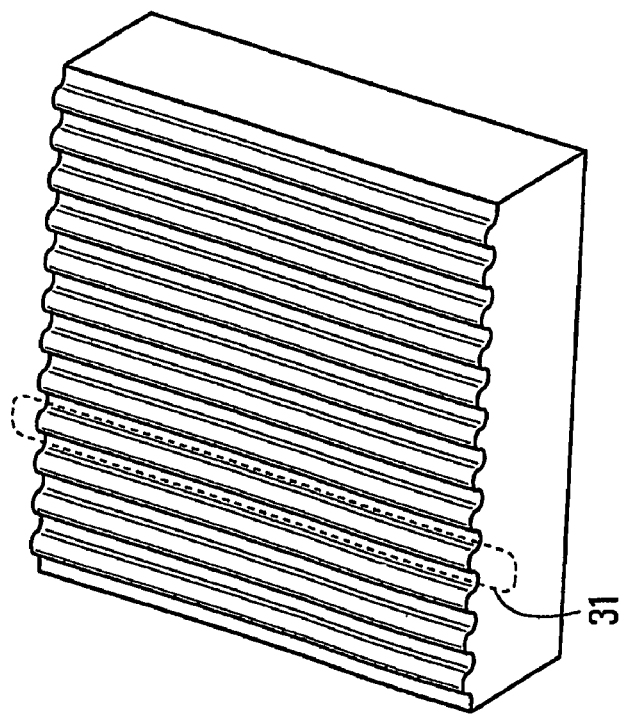

With reference to FIG. 1, there is shown a microfluidic separation system 10, which includes a magnetic separator 12 and a microfluidic chip 14. The magnetic separator 12 includes a first magnetically conductive member 16 and a second magnetically conductive member 18. Also provided is a magnetic energy source 20 that is connected to the first and second members 16, 18. In some non-limiting embodiments, the magnetic energy source 20 may be a permanent magnet or an arrangement (e.g., a stack) of permanent magnets. Non-limiting examples of suitable permanent magnets are those made from a rare earth material, such as Nd—Fe—B. In other non-limiting embodiments, the magnetic energy source 20 may be an electromagnet subjected to direct current (DC) or alternating current (AC). The strength of the magnetic energy source 20 is not particularly limited. For example, a suitable minimum value for the maximum magnetic energy is 40 MGOe (mega giga oersteds), although other values for the magnetic energy are within the scope of the present invention.

In a specific non-limiting embodiment, the first and second members 16, 18 can be made from low carbon steel with high magnetic conductivity and high magnetic saturation. Other possibilities are of course within the scope of the present invention. The first member 16 and the second member 18 are coupled to the magnetic energy source 20. Where the magnetic energy source 20 exhibits a pair of poles, each of the members 16, 18 can be coupled to a corresponding one of the poles. Specifically, a certain surface area A1 of each of the members 16, 18 is in contact with the magnetic energy source 20. The members 16, 18 form a pair of arms whose respective terminal ends 22, 24 do not meet but rather are separated by a gap 26. By virtue of the magnetic conductivity of the members 16, 18 and their contact with the magnetic energy source 20, a magnetic field will be applied across the gap 26 due to the magnetic energy source 20.

In some embodiments, such as the one shown in FIG. 1, either or each of the first and second members 16, 18 may be constructed from an integral piece of magnetically conductive material, in which case the portions of the first and second members 16, 18 carrying terminal ends 22, 24 will be designed to have a cross-sectional area A2 less than A1, namely the area of the first and second members 16, 18 that is in contact with the magnetic energy source 20. In other embodiments, the first and second members 16, 18 may each be constructed from multiple segments (also referred to as "yokes") of magnetically conductive material that are coupled together. In this case, those segments carrying the terminal ends 22, 24 will be designed to have a cross-sectional area less than the area of the first and second members 16, 18 that is in contact with the magnetic energy source 20.

Furthermore, an alignment spacer 5 may be provided to properly separate the first and second members 16, 18 and prevent their respective terminal ends 22, 24 from moving towards each other—and the gap 26 from closing—under the force arising from the magnetic field applied across the gap 26.

To achieve a stronger magnetic field gradient within the gap 26, and therefore improved particle separation of a test sample (e.g., in liquid, gaseous or gel form) circulating within the microfluidic chip 14 when the latter is placed within the gap 26, the terminal end of at least one of the members 16, 18 can be machined or worked so that its surface profile exhibits a pattern of relief elements 31. Specifically, FIGS. 2A-2F show example surface profiles for the terminal end of at least one of the members 16, 18. Suitable example surface profiles include undulating, square-wave or saw-tooth corrugations having elongate ridges alternating with elongate valleys, as well as two-dimensional arrangements of peaks and valleys. Other surface profiles exhibiting patterns of relief elements 31 are of course possible without departing from the scope of the present invention. It should be appreciated that the terminal ends 22, 24 of both members 16, 18 may have surface profiles exhibiting respective patterns of relief elements 31 that are mirror images of one another (vis-à-vis a horizontal plane passing through the gap 26).

Figure 3:
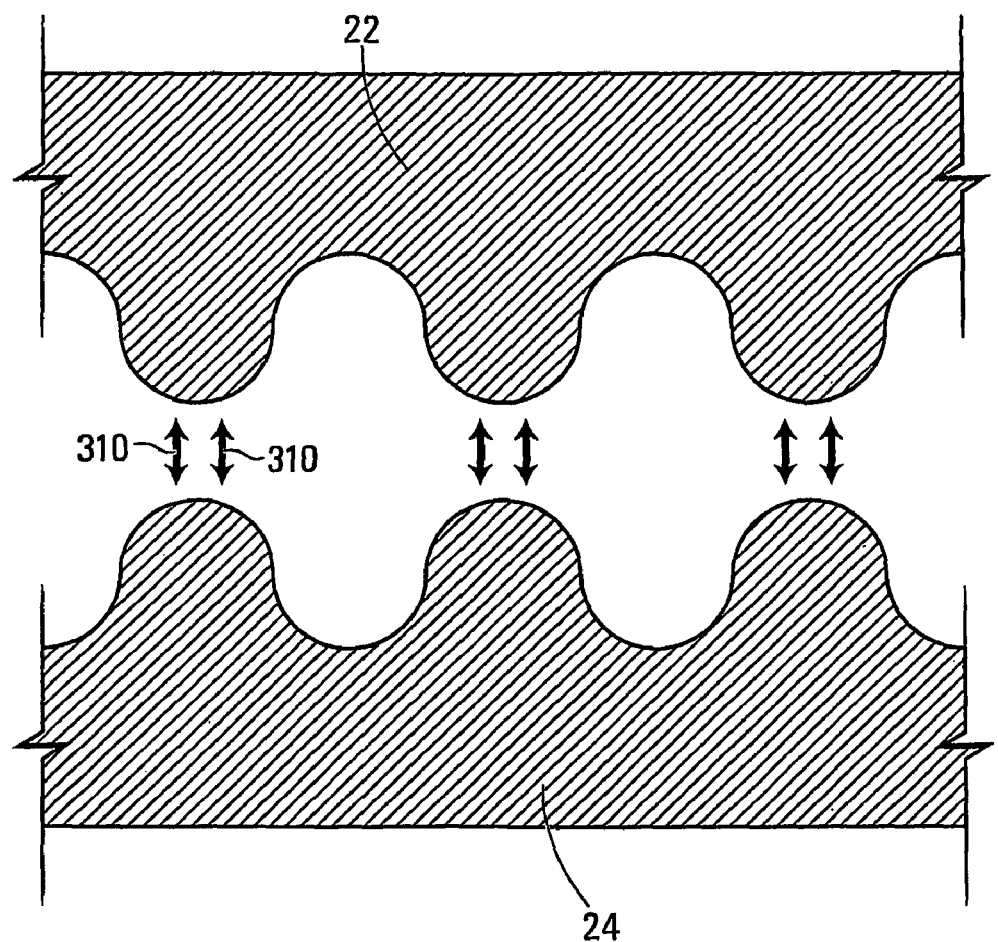
FIG. 3 shows a variation of magnetic field strength laterally across the gap in the orientation of FIG. 1.

It will be noted that the cross-sectional area of the terminal ends 22, 24, which is already smaller than the surface area of the members 16, 18 that is in contact with the magnetic energy source 20, is even smaller at the tips of the relief elements 31. As a result, the applied magnetic field is focused, i.e., the field across the gap 26 is stronger in the area of the peaks and weaker in the area of the valleys. FIG. 3 shows a cross-sectional view (along the x-z plane) of a simulation of magnetic field strength across the gap 26, from which it can be observed that the magnetic field is markedly stronger where the gap 26 is narrower (i.e., between opposing peaks on the surface of the terminal ends 22, 24) than where the gap 26 is wider (i.e., between opposing valleys on the surface of the terminal ends 22, 24). In particular, lines 310 of strong magnetic field are created between opposite peaks of the relief elements 31 on the surfaces of the terminal ends 22, 24.

Figure 4:
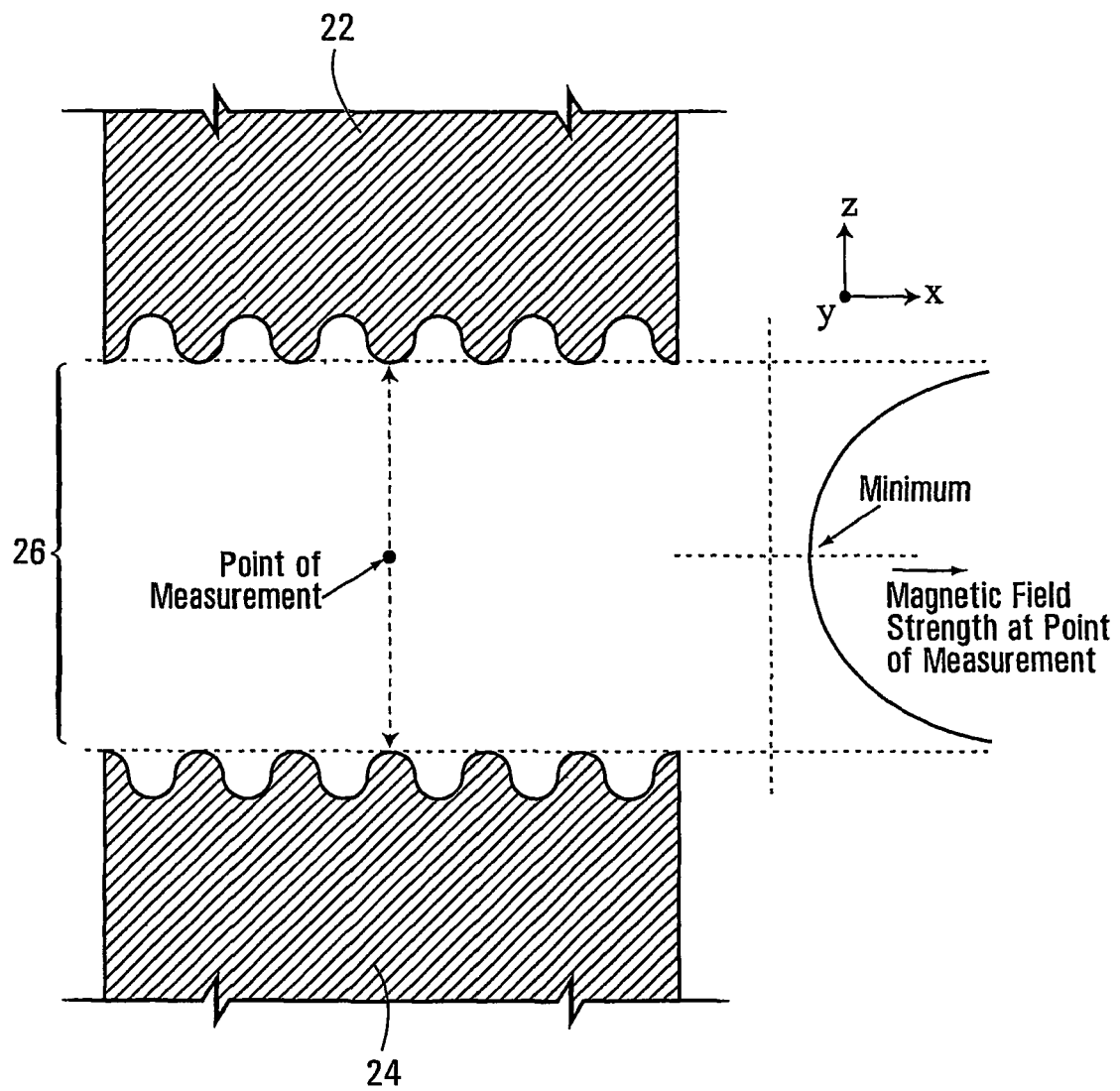
FIG. 4 shows a variation of magnetic field strength vertically across the gap in the orientation of FIG. 1.

Thus, the strength of the applied magnetic field varies laterally (in the x- and y-directions, see FIG. 1) due to the existence of a pattern of relief elements 31 on one or both of the terminal ends 22, 24, which leads to sharper variations of the magnetic field within the gap 26 (i.e., a stronger magnetic field gradient) than in the case of flat terminal ends 22, 24. In addition, the strength of the applied magnetic field also varies according to where in the gap 26 the microfluidic chip 14 is placed in the z-direction, i.e., as a function of distance from the terminal ends 22, 24. Specifically, with reference to FIG. 4, the magnetic field along the z-direction for a particular point in the gap 26 is seen to decrease from maximum values near the top and bottom of the gap 26, to a minimum value at the center of the gap 26. Therefore, the applied magnetic field will be weakest towards the middle of the gap 26 (in, the z-direction) and strongest towards either of the terminal ends 22, 24.

Figure 5A:
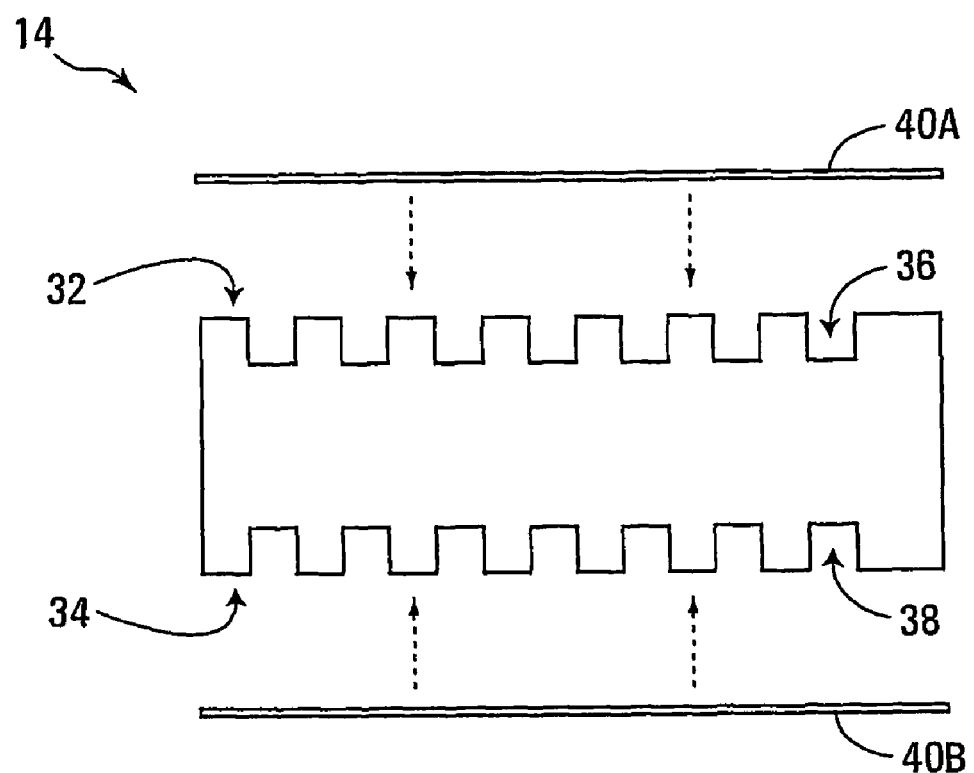
FIGS. 5A-5C are, respectively, an exploded cross-sectional view, a bottom view and an exploded perspective view of the microfluidic chip, in accordance with a non-limiting embodiment of the present invention.
Figure 5B:
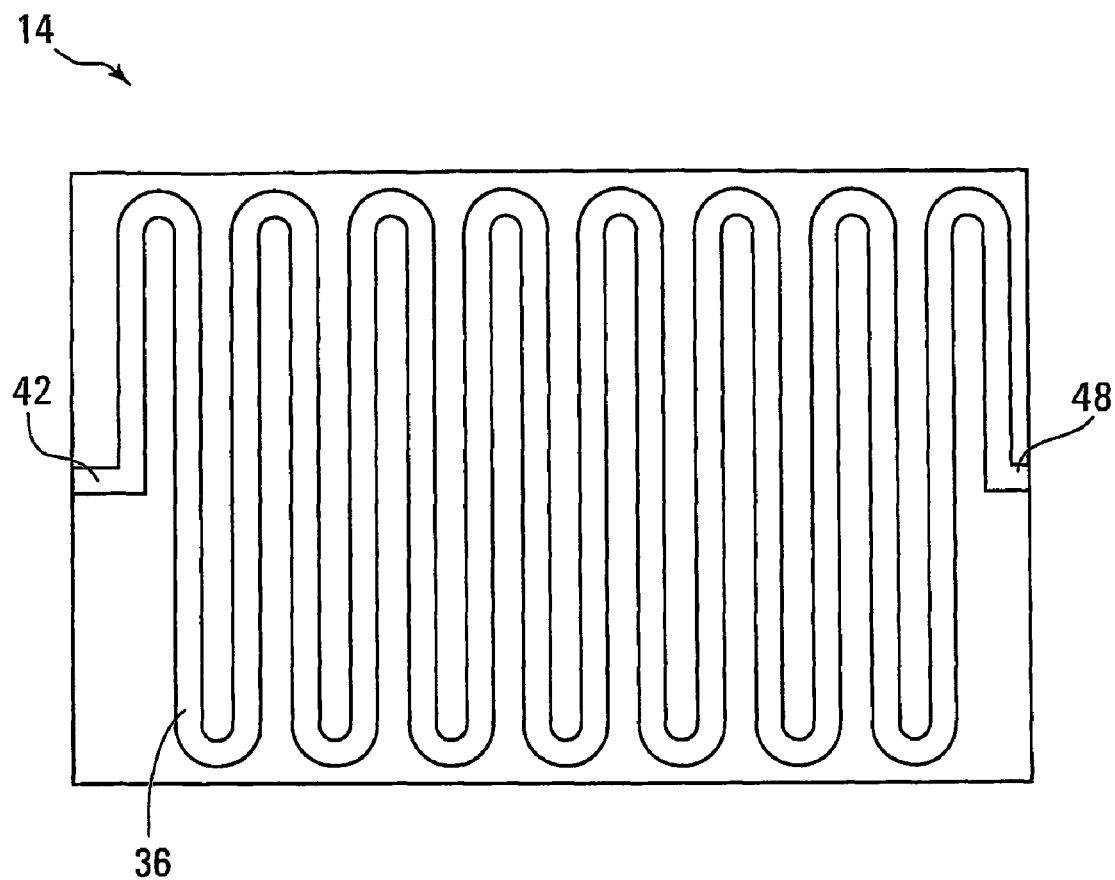
Figure 5C:
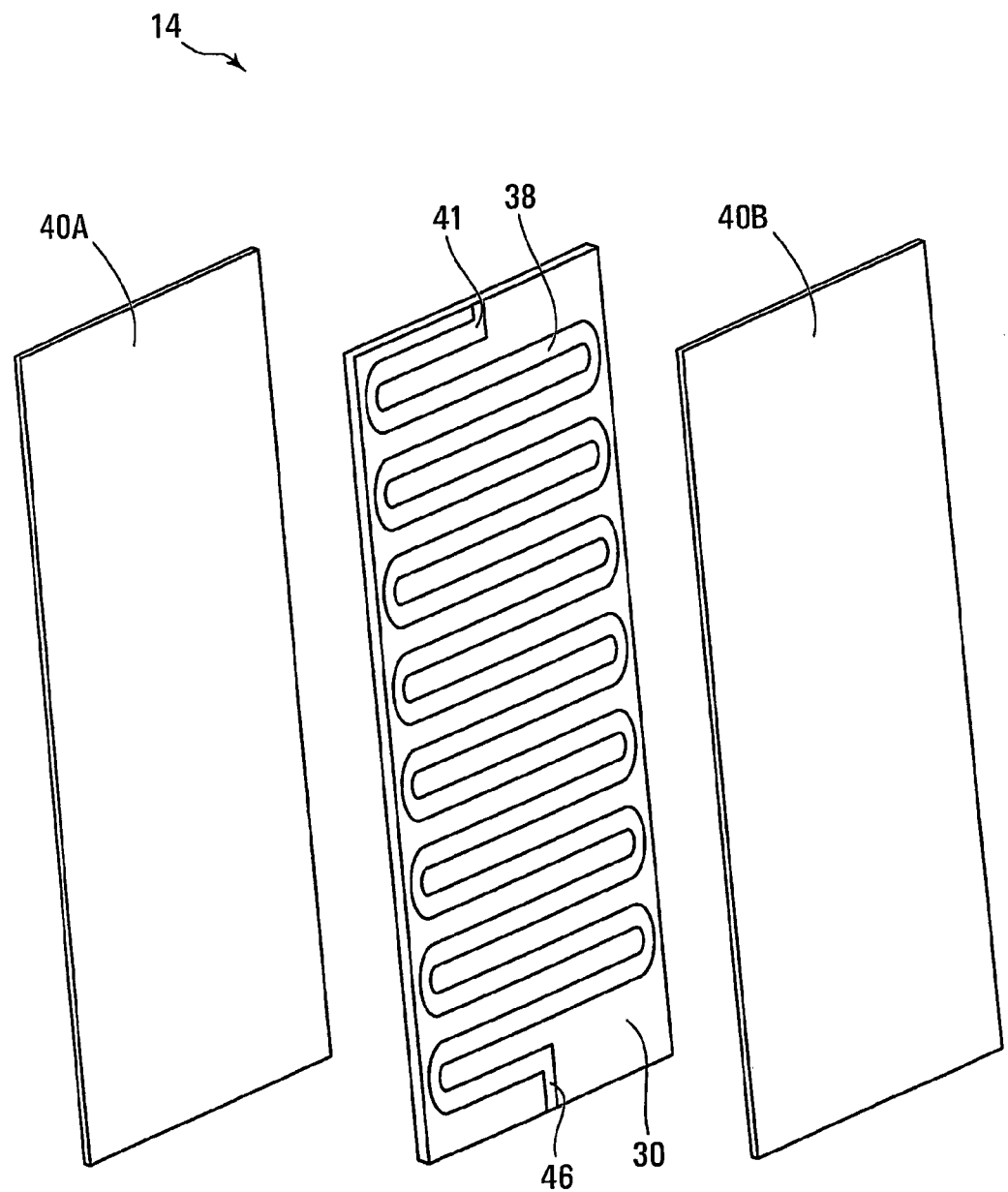

Referring again to FIG. 1, and with additional reference to FIGS. 5A-5C, the microfluidic chip 14 is now described. The chip 14 includes a body 30 defining a plurality of channels on respective faces of the body 30. The body 30 may be made of a material having high magnetic conductivity (e.g., low carbine steel, silicon steel), although this is not a requirement of the present invention, since other materials (e.g., polymeric material such as polycarbonate or polymethyl methacrylate plastic, as well as glass or silicon) can also be used with success. In a specific non-limiting embodiment, the body 30 may have two opposite planar faces 32, 34, with respective channels 36, 38 being defined on the two faces 32, 34. In particular, channel 36 is on face 32 and channel 38 is on face 34. The channels 36, 38 may be constructed in a variety of ways. Techniques such as injection molding, embossing, cutting, machining and micromachining could be used for this purpose. For example, the channels 36, 38 may be carved (e.g., etched or machined) into a surface of the body 30 from either face or they may be built up (e.g., grown or deposited) onto the surface of the body 30. Still other techniques are within the scope of the present invention.

An exterior lining 40A, 40B is provided so as to seal the channels 36, 38, allowing separate test sample volumes to be retained within the channels 36, 38 on either face of the chip 14. The exterior lining 40A, 40B can be made of one or more thin layers of polyethylene (PET) or other suitable material. The exterior lining 40A, 40B could be rigid (e.g., in the form of a plate) or flexible (e.g., in the form of a membrane). In various non-limiting embodiments, the exterior lining 40A, 40B may be composed of a single piece that is wrapped wholly around the body 30 or it may be composed of separate components, each of which seals a respective one of the channels 36, 38. An example thickness for the exterior lining 40A, 40B that may be suitable is 0.05 to 0.10 mm, but this is not to be considered a limitation of the present invention, as other thicknesses are, possible. The exterior lining 40A, 40B may also be in the form of a tape.

Each of the channels 36, 38 has the capacity to carry a test sample from a respective one of a plurality of inlet ports 41, 42 to a respective one of a plurality of outlet ports 46, 48. It should be appreciated that the two channels 36, 38 on either face of the body 30 may, but need not be, mirror images of one another.

A test sample can be supplied to a particular one of the channels 36, 38 and drawn therefrom. For example, a pump (e.g., a computer-controlled syringe pump) can be used to supply a test sample into channel 36 via inlet port 41 and draw the test sample from outlet port 44. In addition, a test sample can be pumped into channel 38 via inlet port 42 and drawn from outlet port 46.

In another example, the test samples can be loaded into the channels 36, 38 by gravity. Specifically, with reference to FIGS. 12A-12C, there is provided a respective container 1202A, 1202B, 1202C that supplies, by gravity, a test sample to a channel formed in the body of a respective microfluidic chip 1214A, 1214B, 1214C. The test sample is drawn, also by gravity, from a respective outlet port 1246A, 1246B, 1246C. This embodiment could work with the magnetic separator 12 of FIG. 1 if it were rotated a quarter-turn to orient the gap 26 horizontally rather than vertically.

In an embodiment, two test samples from the same source are circulated through the two channels 36, 38. In another embodiment, the two test samples are from different sources. In yet another embodiment, outlet port 44 is connected to inlet port 42 (e.g., using a via through the body 30) such that the same test sample will circulate through channel 36 and then through channel 38.

In some cases, the channels 36, 38 exhibit parallel elongate traces in a "plane of flow", with the ends of ones of the traces being joined respectively to the beginnings of others of the traces by respective 180-degree bends. Here, the given test sample can follow a pre-determined, meandrous flow path in the plane of flow.

Figure 12A:
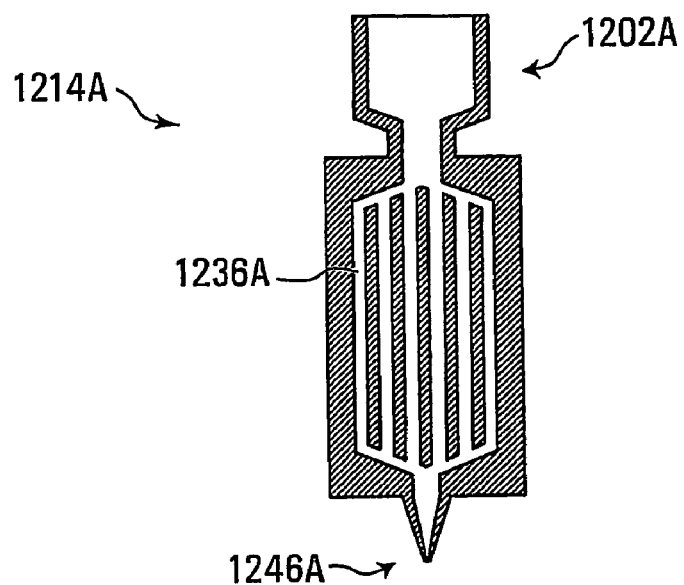
FIGS. 12A-12C show various possibilities for a microfluidic chip in accordance with alternative embodiments of the present invention, wherein a container is provided for supplying a test sample to the chip.

In other cases, the channels 36, 38 exhibit parallel elongate traces in a "plane of flow", with such traces meeting at the respective inlet port 41, 42 and also at the respective outlet port 44, 46 (such as in the embodiment of FIG. 12A). Here, a given test sample in a given one of the channels 36, 38 does not follow a pre-determined flow path, as several options are possible for the given test sample to travel from the respective inlet port 41, 42 to the respective outlet port 44, 46. The channels 36, 38 can be designed to provide other configurations of the flow path within the plane of flow without departing from the scope of the present invention.

In operation, the chip 14 is inserted into the gap 26. Of course, the gap 26 has to be sufficiently wide to accommodate the chip 14. In some embodiments, the gap 26 and the chip 14 are dimensioned so that when the chip 14 is placed into the gap 26, the exterior lining 40 of the chip 14 contacts the terminal ends 22, 24 of the members 16, 18, effectively causing the chip 14 to be retained within the gap 26 by the relief elements 31 at the terminal ends 22, 24 of the members 16, 18. In an alternate embodiment, at its narrowest point the gap 26 can be wider than the chip 14, and a holder external to the magnetic separator 12 can be provided. The chip 14 is slid into the gap 26 until it reaches and engages the holder; when the chip 14 is released it will be held within the gap 26 by the holder.

Figure 6:
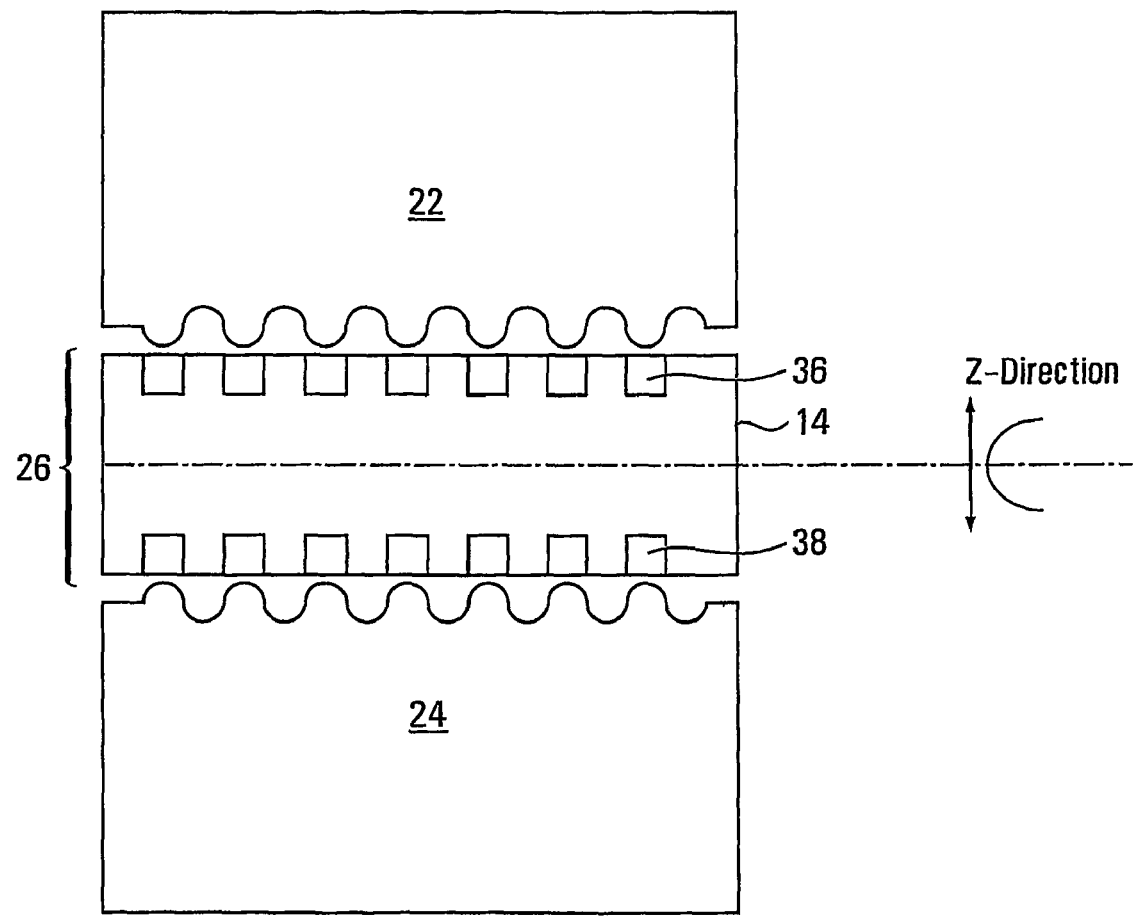
FIG. 6 is a cross-sectional view of the microfluidic chip upon insertion into the gap, illustrating the presence of channels on either of two faces of the microfluidic chip.

With reference now to FIG. 6, it will be observed that once the chip 14 is inserted into the gap 26, channel 36 will be offset from the center of the gap 26 (in the z-direction) such that it is closer to terminal end 22, while channel 38 will also be offset from the center of gap 26, but will be closer to terminal end 24. Thus, the test sample in channel 36 will be confined to circulating closer to terminal end 22, while the test sample in channel 38 will be confined to circulating closer to terminal end 24. It is noted that since there is little or no test sample volume circulating at the center of the gap 26 (in the z-direction), this means that little or no test sample volume will circulate in a plane of the z-direction where the applied magnetic field is weakest. Instead, most of the test sample is forced to circulate in planes of the z-direction where the applied where magnetic field is above its minimum value. Those skilled in the art will appreciate that where one wishes to achieve a requirement where at least X percentage of the test sample volume is to be exposed to a magnetic field of no less than Y times its minimum value, for particular values of X and Y, then techniques such as analytical modeling, simulation and/or experiment can be employed to determine suitable dimensions and configurations of the chip 14, relief elements 31 and applied magnetic field.

It should be appreciated that in the special case where a given one (or both) of the channels 36, 38 exhibits generally parallel elongate traces (whether or not they are joined by 180-degree bends) in a plane of flow, the traces can be specifically designed to have a relationship with the lines 310 of strong magnetic field.

Figure 7A:
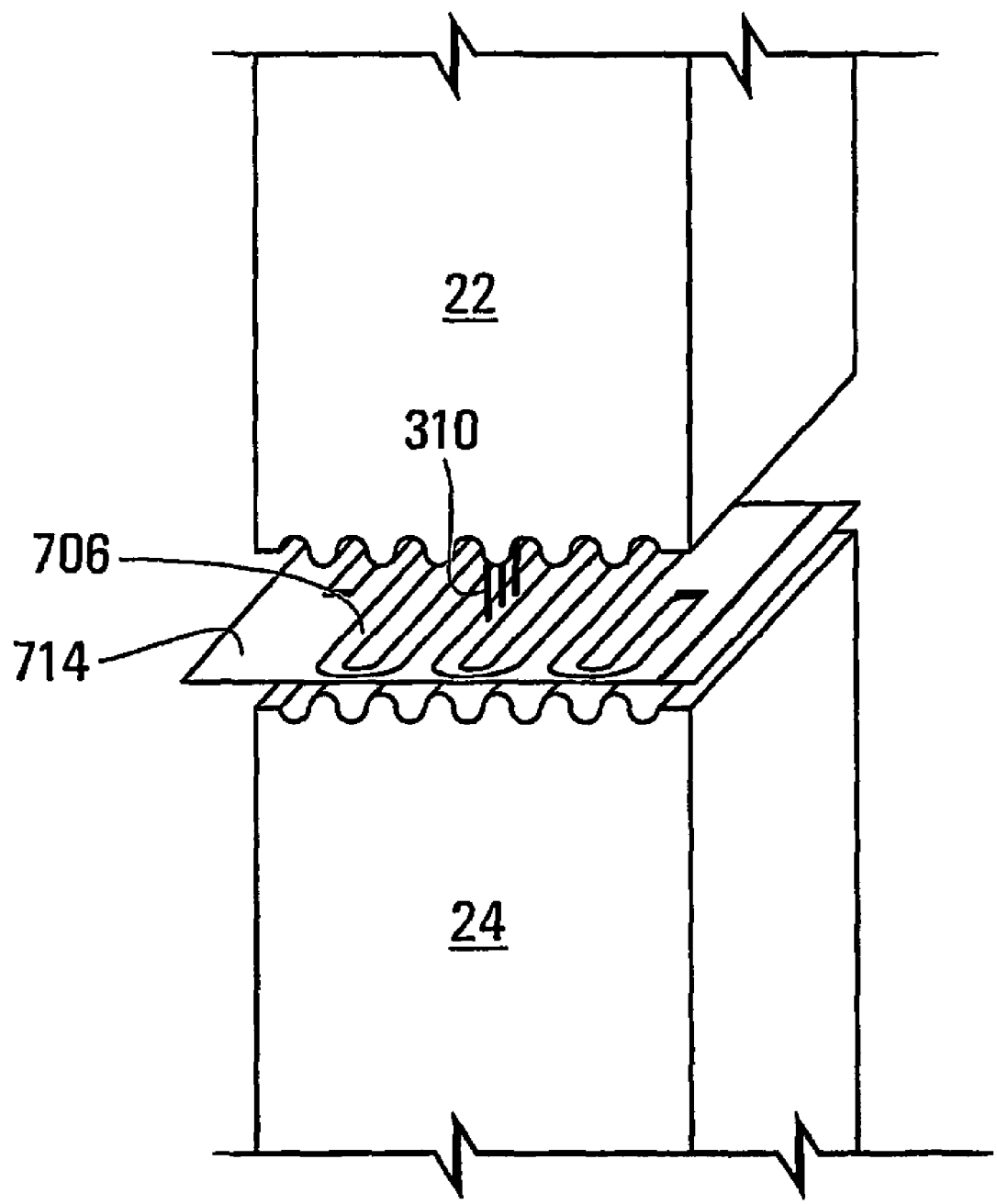
FIG. 7A is a perspective view of the microfluidic chip upon insertion into the gap, where the microfluidic chip in this particular figure is designed to include a channel formed of elongate traces that are aligned with lines of strong magnetic field exerted by the gap.

For example, with reference to FIG. 7A, there is shown insertion into the magnetic separator 12 of the chip 714 that is generally planar and is generally in the center of the gap 26 (in the z-axis). The chip 714 has been designed with elongate traces 706 in a plane of flow. Certain ones of these traces 706 are aligned with the lines 310 of strong magnetic field as projected onto the plane of flow.

Figure 7B:
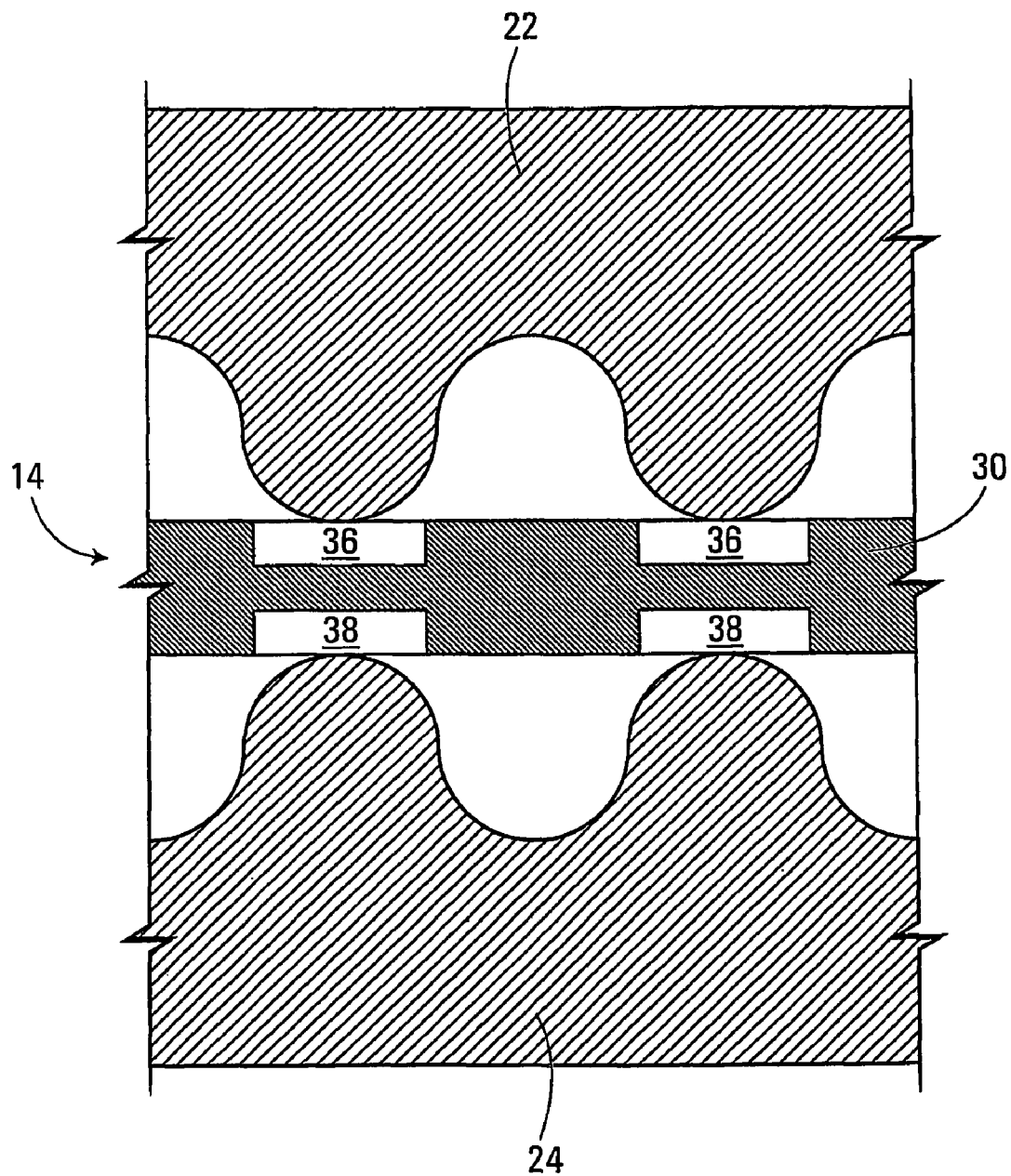
FIG. 7B is a cross-sectional view through the terminal ends, the gap and the microfluidic chip of FIG. 7A, showing the presence of channels on either of two faces of the microfluidic chip.

FIG. 7B illustrates a cross-section through the terminal ends 22, 24, the gap 26 and the body 30, showing the two channels 36, 38 on either face of the body 30. It is noted that the test sample volumes in both channels 36 and 38 are subjected to a magnetic field that is stronger than it would have been if the test sample had been allowed to travel along a single channel passing through the center of the body 30.

Figure 12B:
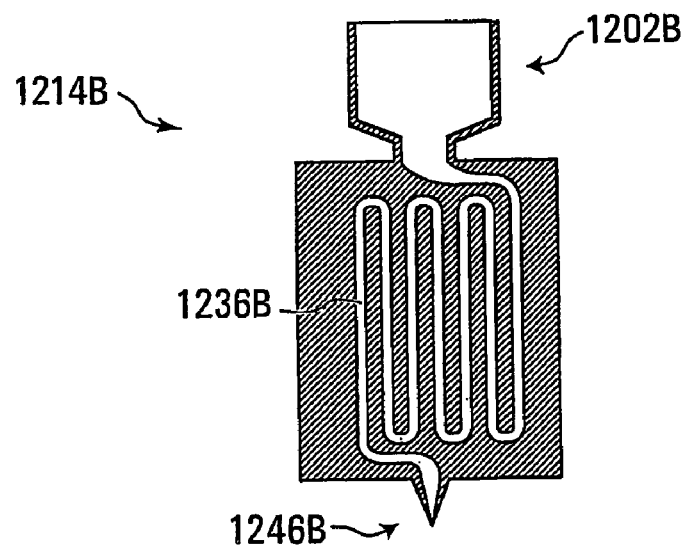

A similar effect may be achieved using the microfluidic chips 1214A, 1214B of FIGS. 12A and 12B, which has been designed with respective elongate traces 1236A, 1236B in a respective plane of flow, certain ones of which can be aligned with the lines 310 of strong magnetic field as projected onto the respective plane of flow.

Figure 8A:
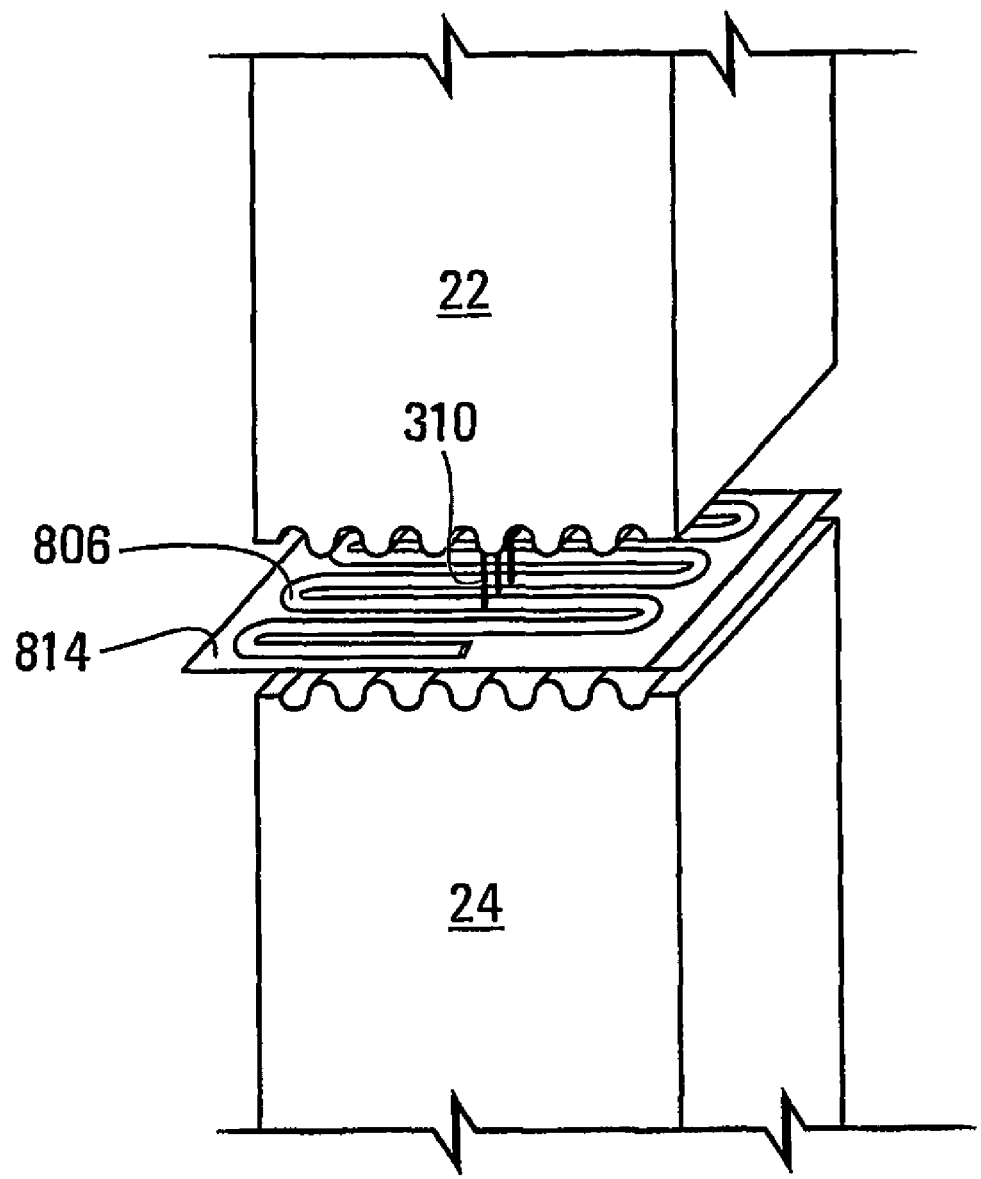
FIG. 8A is a perspective view of the microfluidic chip upon insertion into the gap, where the microfluidic chip in this particular figure is designed to include a channel formed of elongate traces that are orthogonal to lines of strong magnetic field exerted by the gap.

In an alternate embodiment, with reference to FIG. 8A, there is shown insertion into the magnetic separator 12 of a chip 814 that is also generally planar. The chip 814 has been designed with elongate traces 806 in a plane of flow. Certain ones of the traces 806 cross multiple ones of the lines 310 of strong magnetic field as projected onto the plane of flow.

Figure 8B:
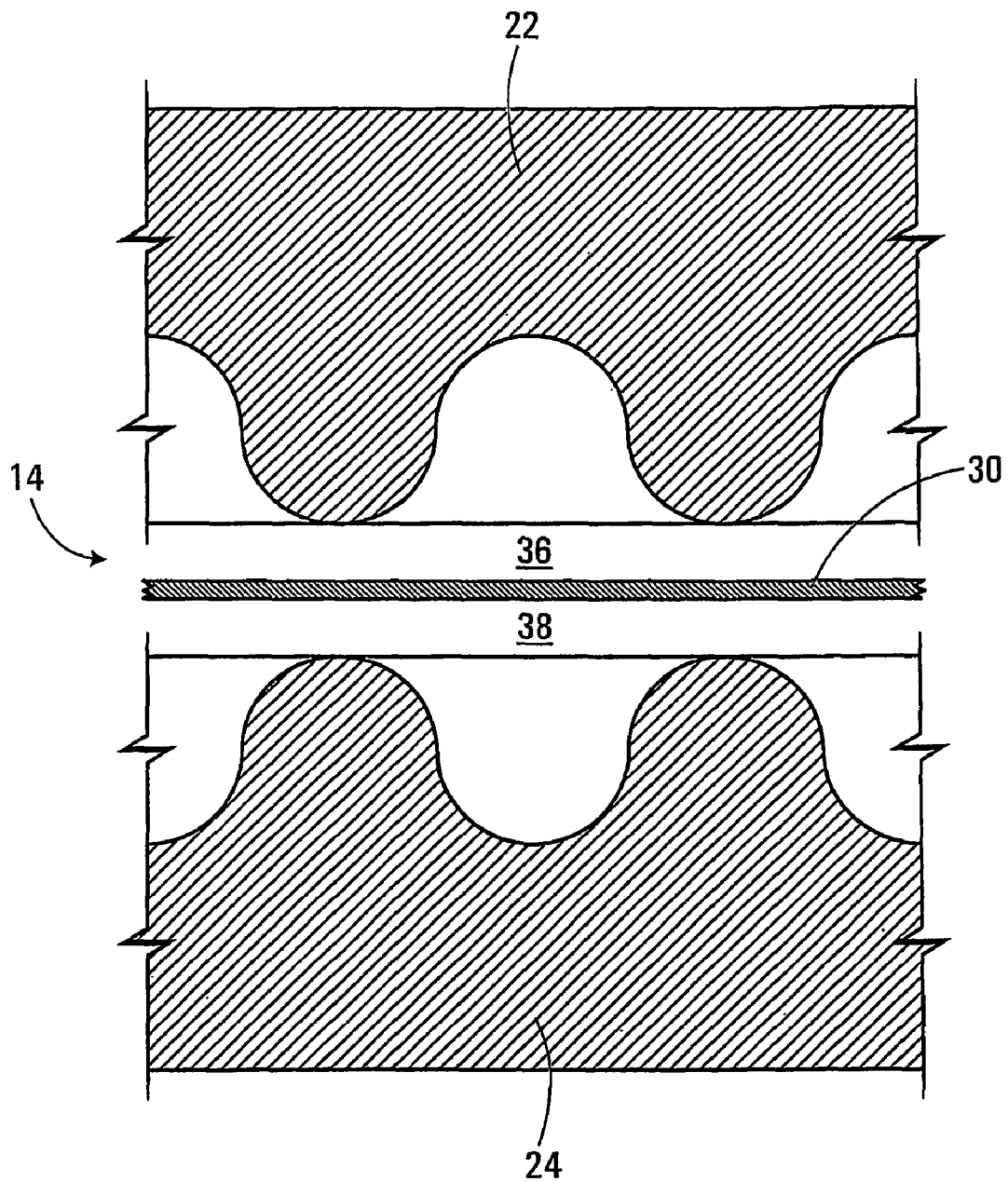
FIG. 8B is a cross-sectional view through the terminal ends, the gap and the microfluidic chip of FIG. 8A, showing the presence of channels on either of two faces of the microfluidic chip.

FIG. 8B illustrates a cross-section through the terminal ends 22, 24, the gap 26 and the body 30, showing the two channels 36, 38 on either face of the body 30. It is noted that despite the different orientation of the traces in FIG. 8A when compared to those of FIG. 7A or FIG. 12A, the test sample volumes in both channels 36 and 38 are still nevertheless subjected to a magnetic field that is stronger than it would have been if the test sample had been allowed to travel along a single channel passing through the center of the body 30.

Figure 12C:
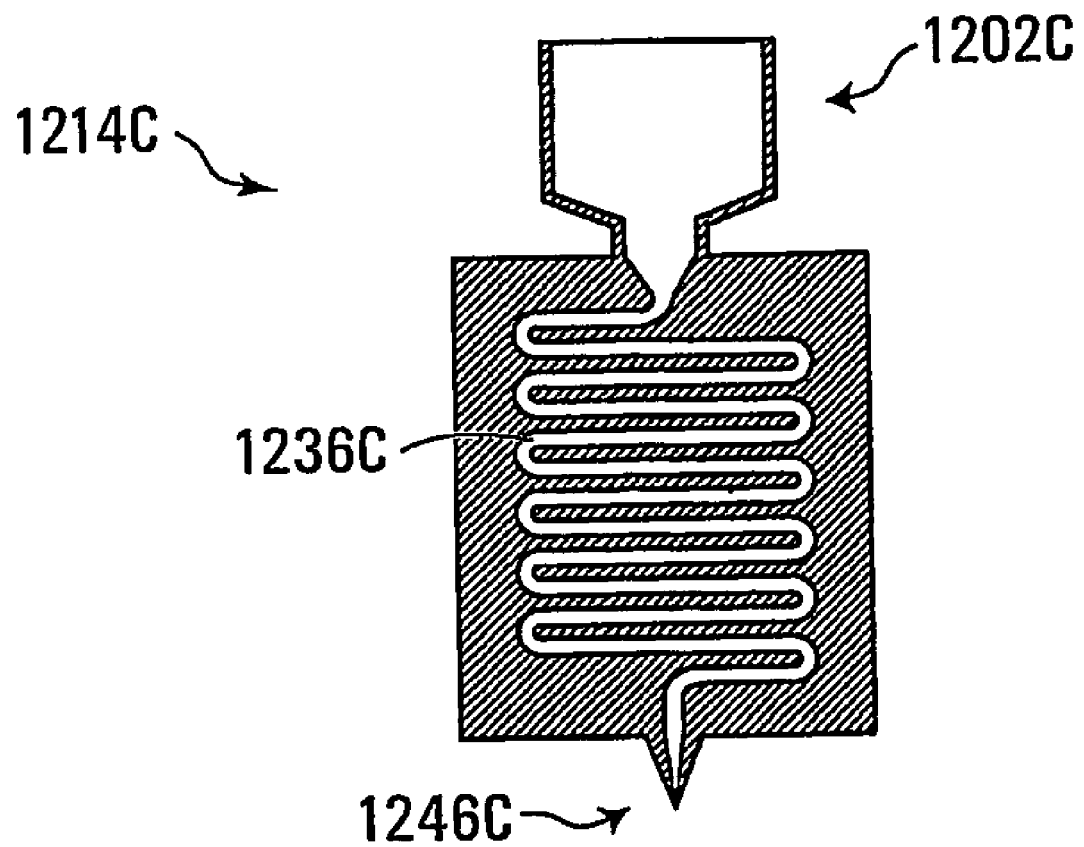

A similar effect may be achieved using the chip 1214C of FIG. 12C, which has been designed with elongate traces 1236C in a plane of flow, certain ones of which cross multiple ones of the lines 310 of strong magnetic field as projected onto the plane of flow.

Non-limiting examples of application of the microfluidic separation system 12 include the separation and/or enrichment of target material from biological test samples such as blood samples, bacterial and/or cell suspensions or extracts, protein or antibody solutions and various buffers.

In a specific example of application, the cultured Human Hepatocellular Carcinoma cell (HepG2) was used as the target cell for a cell separation experiment. The cell was labeled with magnetic nanoparticles with a diameter of 10 nm. These nanoparticles fluoresce in nature. The labeled HepG2 was mixed with non-labeled fresh human red blood cells. The ratio of HepG2 to red blood cells was 10%. The cell mixture was suspended in a separation buffer containing 2% fetal bovine serum and 1 mM EDTA in phosphate buffered saline (PBS). The final total cell concentration is adjusted to $1\times10^7$ cell/ml. The separation results are analysed by using flow cytometry.

For the separation efficiency study, flow rates of 100-500 μl/min controlled by syringe pump were used. A chip in accordance with an embodiment of the present invention was inserted to the gap (previously labeled 26). The cell mixture was supplied to the chip. The target cells (labeled with magnetic nanoparticles) were trapped inside the channels (previously labeled as 36, 38) due to the high-intensity/high-gradient magnetic field, while non-labeled "debris cells" flowed out the separation chip. After the cell mixture fully passed through the separation chip, 5 ml of 1×PBS was used to flush the separation channel at a flow rate of 500 μl/min. This process washes out the un-trapped cells in the channel of the chip. Finally, the chip was taken out from the separation gap. The trapped cells were flushed out by using 1×PBS at a flow rate of 1 ml/min.

Figure 9A:
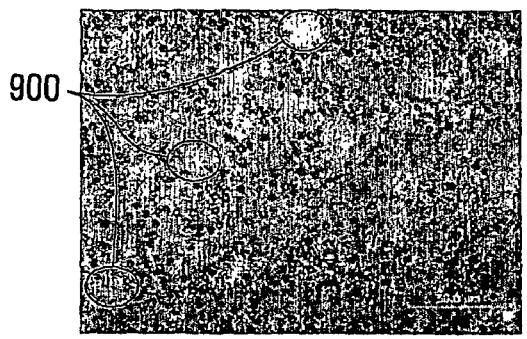
FIG. 9A shows an optical image of a test sample before separation by a microfluidic chip in accordance with an embodiment of the present invention.
Figure 9C:
FIGS. 9B-9D show optical images of the test sample of FIG. 9A after separation by the microfluidic chip at various flow rates.
Figure 9B:
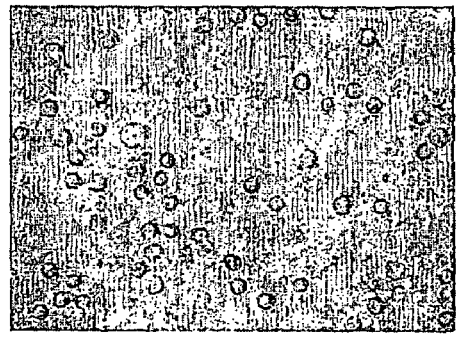
Figure 9D:
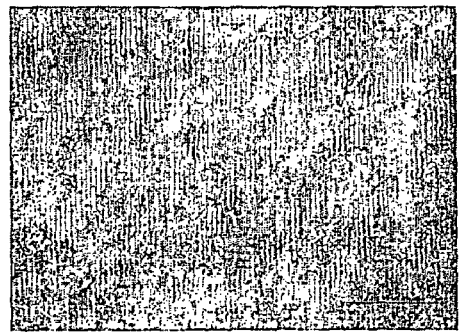

FIG. 9A shows the optical image of cells before separation under fluorescence microscope under 365 nm UV light excitation. The target cells (i.e., those labeled with magnetic nanoparticles) are easy to identify under the microscope because of their fluorescence, and some are labeled as 900 in FIG. 9A for convenience. It is noted that the target cells are present among a greater number of non-target cells. In contrast, FIGS. 9B-9D show the optical image of cells after separation under the same optical conditions, demonstrating a certain degree of purity of the target cells. The difference between FIGS. 9B, 9C and 9D is the flow rate through the chip, which was 2000 μl/min, 300 μl/min and 400 μl/min, respectively.

Figure 13A:
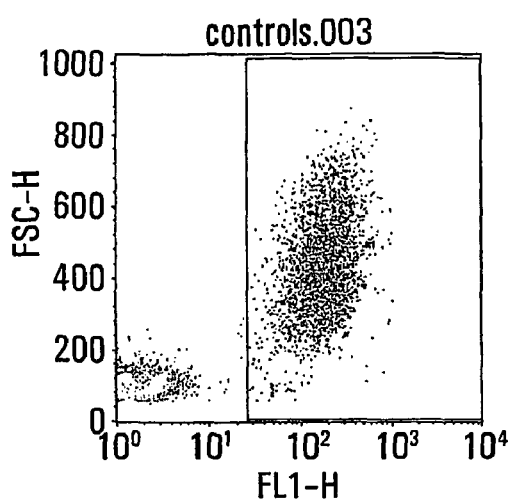
FIGS. 13A-13D illustrate purity of the test sample illustrated in FIGS. 9A-9D, respectively, obtained by flow cytometry.
Figure 13C:
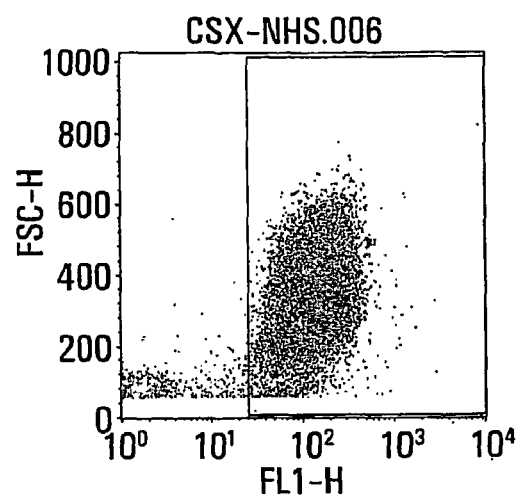
Figure 13B:
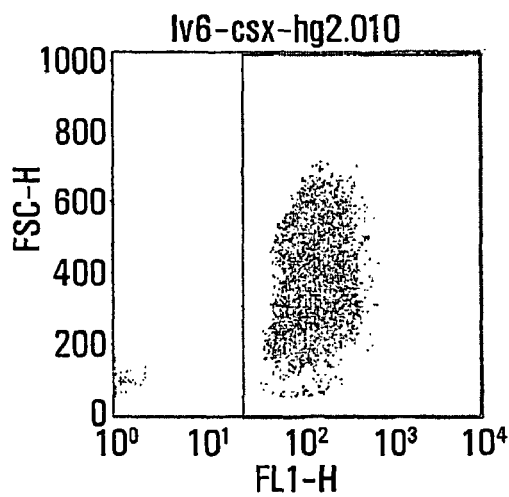
Figure 13D:
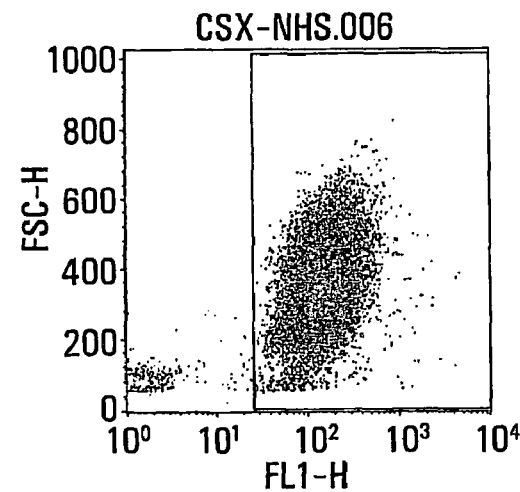

The purity of the separated target cells was analyzed by flow cytometry and is illustrated in FIGS. 13A-13D. Specifically, the result for the original cell mixture (refer to FIG. 9A) is shown in FIG. 13A, recalling that the percentage of HepG2 cells was 10% before separation. FIGS. 13B, 13C and 13D show the separation results for the above mentioned flow rates of 200 μl/min, 300 μl/min and 400 μl/min, respectively (refer to FIGS. 9B, 9C and 9D).

Figure 10:
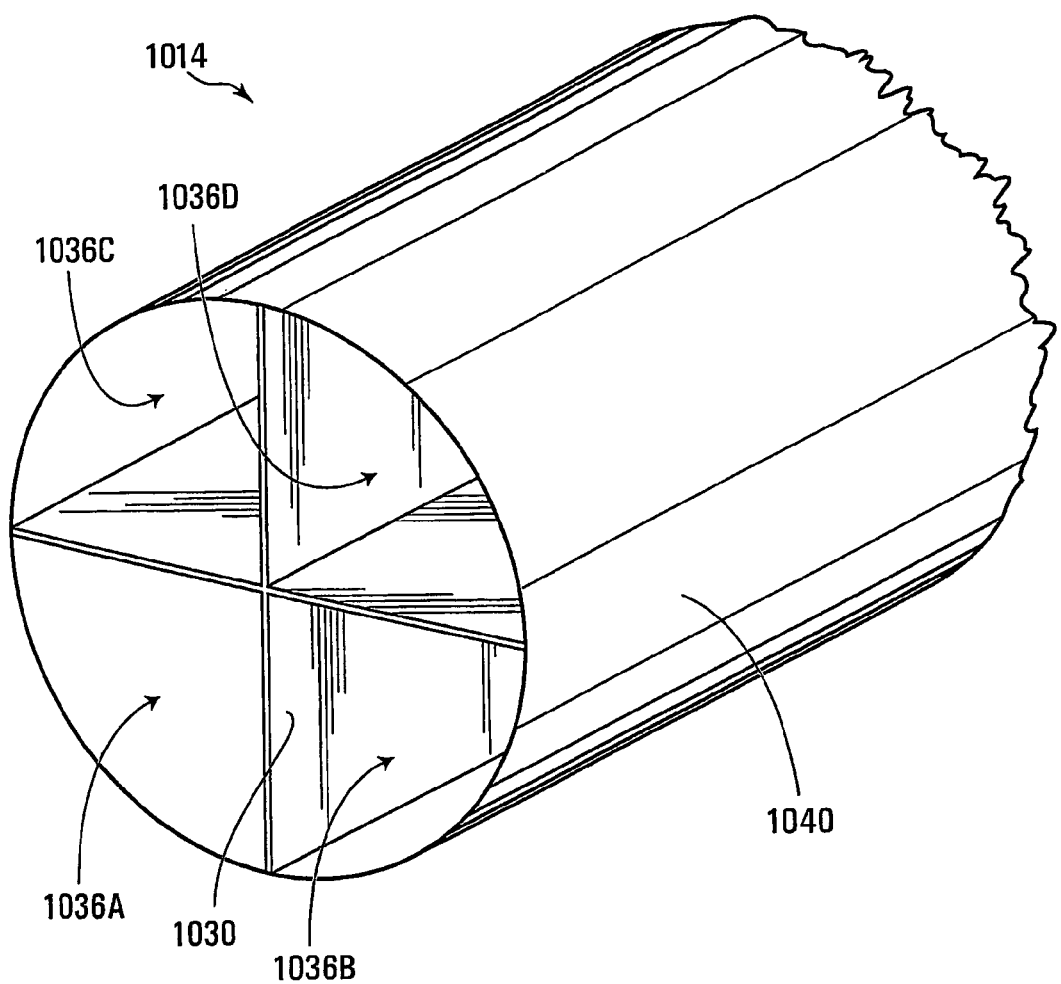
FIG. 10 is a perspective view of a microfluidic chip illustrating an alternative design with four angularly distributed channels.
Figure 11:
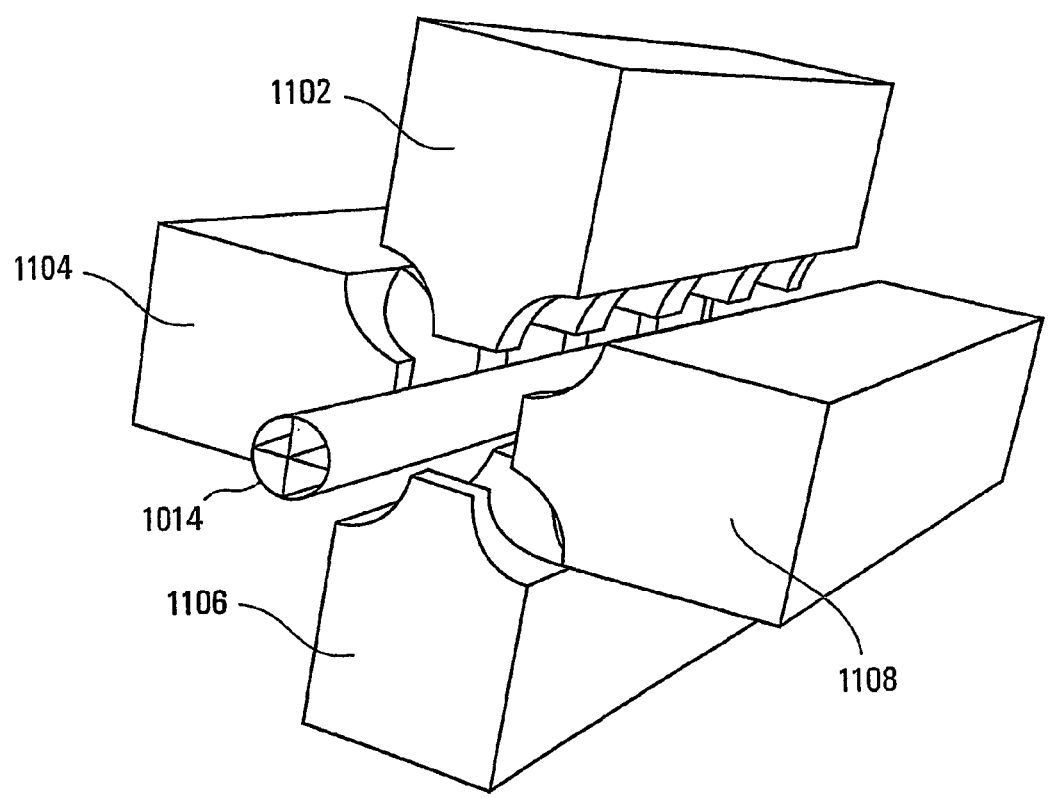
FIG. 11 is a perspective view of a magnetic separator designed to accommodate the microfluidic chip of FIG. 10.

Those skilled in the art will appreciate that although the chip 14 has been described whose body 30 is generally planar, it is nevertheless possible to design other chip shapes without departing from the scope of the present invention. In particular, FIG. 10 shows a microfluidic chip 1014 designed as a cylinder with a body 1030 defining four (4) angularly distributed channels 1036A, 1036B, 1036C, 1036D on respective curved faces of the body 1030, although the faces need not be curved (and therefore the body 1030 need not be cylindrical) in all embodiments. An exterior lining 1040 forms a sheath of the cylinder. The four channels 1036A, 1036B, 1036C, 1036D, each generally forming an elongate wedge, allow four separate test sample volumes to pass through the chip 1014. Such an arrangement may be particularly useful where, as shown in FIG. 11, the magnetic separator 1112 is designed to have a four-pole design, namely, with two pairs of opposite-ended poles (1102/1106 and 1104/1108) arranged in such a way as to leave a passageway for insertion of the chip 1014. In this way, up to four individual test sample volumes can be subjected to magnetic separation simultaneously.

Those skilled in the art will appreciate that strong magnetic forces may be obtainable because of the comparatively higher field density and gradient of field density provided by certain embodiments of the microfluidic separation system of the present invention. This allows improved separation and/or extraction to be achieved with finer magnetic particles such as magnetic nanoparticles and magnetic quantum dots. Moreover, the microfluidic chip 14 has a simple structure, offering lower costs and higher efficiency when compared to conventional technologies. Also, the planar channels 36, 38 in the body 30 provide the microfluidic chip 14 with a small dead volume, thus enabling the processing of smaller test sample volumes and making the system suitable for the purification of rare or costly samples, such as stem cells for example.

While specific embodiments of the present invention have been described and illustrated, it will be apparent to those skilled in the art that numerous modifications and variations can be made without departing from the scope of the invention as defined in the appended claims.

What is claimed is:

1. A microfluidic separation system, comprising:
  a magnetic separator, comprising:
    a. a magnetic energy source;
    b. first and second magnetically conductive members leading from the magnetic energy source and having respective terminal ends; and
    c. the terminal ends of the first and second members being separated by a gap over which a magnetic field is applied due to the magnetic energy source, the magnetic field decreasing from the terminal ends towards an area of minimum field between the terminal ends; and
  a microfluidic chip for insertion into the gap, comprising:
    a. a body defining a plurality of channels on respective faces of the body; and
    b. an exterior lining that seals the plurality of channels to allow separate test sample volumes to circulate in at least two of the channels;
  wherein upon insertion of the microfluidic chip into the gap, the area of minimum field is positioned between, and offset from, a first channel on a first face of the body and a second channel on a second face of the body, and a first one of the test sample volumes in the first channel is confined to circulating closer to the terminal end of the first member and a second one of the test sample volumes in the second channel is confined to circulating closer to the terminal end of the second member.

2. The microfluidic separation system defined in claim 1, wherein at least two of the channels are mirror images of one another on respective faces of the body.

3. The microfluidic separation system defined in claim 1, wherein at least two of the channels are not mirror images of one another on respective faces of the body.

4. The microfluidic separation system defined in claim 1, wherein the microfluidic chip includes a respective inlet port and a respective outlet port for each of the channels.

5. The microfluidic separation system defined in claim 1, wherein the microfluidic chip comprises a container for supplying at least one of the test sample volumes into the respective at least one of the channels by gravity.

6. The microfluidic separation system defined in claim 1, wherein the terminal end of at least one of the first and second member exhibits a pattern of relief elements.

7. The microfluidic separation system defined in claim 1, wherein the terminal ends of the first and second members exhibit respective patterns of relief elements.

8. The microfluidic separation system defined in claim 7, wherein the patterns of relief elements are mirror images of one another.

9. The microfluidic separation system defined in claim 7, wherein the patterns of relief elements are corrugations.

10. The microfluidic separation system defined in claim 9, wherein at least one of the channels includes generally parallel elongate traces within a plane of flow.

11. The microfluidic separation system defined in claim 10, wherein the magnetic field exhibits lines of strong magnetic field between tips of the respective corrugations on the terminal ends of the first and second members, and wherein said plane of flow is orthogonal to the lines of strong magnetic field.

12. The microfluidic separation system defined in claim 11, wherein certain ones of the traces are aligned with respective ones of the lines of strong magnetic field as projected onto said plane of flow.

13. The microfluidic separation system defined in claim 12, wherein certain ones of the traces are connected by bends, thereby to establish a meandrous flow path.

14. The microfluidic separation system defined in claim 12, wherein certain ones of the traces cross multiple ones of the lines of strong magnetic field as projected onto said plane of flow.

15. The microfluidic separation system defined in claim 9, wherein at least two of the channels include respective sets of generally parallel elongate traces.

16. The microfluidic separation system defined in claim 1, wherein the first and second terminal ends establish a pair of magnetic poles on opposite sides of the gap and across which the magnetic field is applied.

17. The microfluidic separation system defined in claim 1, wherein each of the first and second members comprises a respective first yoke connected to a respective second yoke, the respective first yoke having a cross-sectional area and being connected to the source of magnetic energy, the respective second yoke exhibiting the respective terminal end of the respective element, the respective terminal end of the respective element having a cross-sectional area less than the cross-sectional area of the respective first yoke.

18. The microfluidic separation system defined in claim 17, further comprising an alignment spacer that prevents the gap from closing under magnetic force from the magnetic energy source.

19. The microfluidic separation system defined in claim 1, wherein the body is planar with two opposing faces.

20. The microfluidic separation system defined in claim 1, wherein said insertion of the microfluidic chip into the gap involves establishing contact between the exterior lining of the chip and the terminal ends of the first and second members, whereby the microfluidic chip is retained by the magnetic separator within the gap when inserted.

21. The microfluidic separation system defined in claim 1, further comprising a holder external to the magnetic separator and configured to retain the microfluidic chip within the gap.

22. A system comprising:
  a magnetic separator comprising a first pole end and an opposing second pole end separated by a gap, for applying a magnetic field across said gap, said magnetic field decreasing from said pole ends towards an area of minimum field between said pole ends; and a microfluidic chip having a first face and an opposite second face, defining a first fluid channel adjacent said first face and a second fluid channel adjacent said second face, said chip inserted into said gap with said area of minimum field being positioned between, and offset from, said first and second channels.

23. The system of claim 22, wherein at least one of said pole ends has a surface pattern of peaks and valleys.

24. The system of claim 22, wherein at least one of said pole ends has a corrugated surface.

25. The system of claim 24, wherein said corrugated surface has tips and at least one of said first and second channels comprises traces patterned to align with said tips.

26. The system of claim 25, wherein said tips and said traces are elongate and generally parallel to one another.

27. The system of claim 26, wherein selected ones of said traces are connected by bends, to establish a meandrous flow path.

* * * * *